(12) United States Patent
Jin et al.

(10) Patent No.: US 8,422,626 B2
(45) Date of Patent: Apr. 16, 2013

(54) COMPUTED TOMOGRAPHY APPARATUS FOR GEOLOGICAL RESOURCE CORE ANALYSIS

(75) Inventors: Jae Hwa Jin, Daejeon (KR); Jun Ho Kim, Mokpo-si (KR); Min Jun Kim, Daejeon (KR); Han Seok Kim, Yongin-si (KR); Chin Kun Park, Yongin-si (KR); Young Duck Jin, Seongnam-si (KR); Myoung Hun Yoon, Seoul (KR)

(73) Assignee: Korea Institute of Geoscience and Mineral Resources (KIGAM), Daejeon (KR)

( * ) Notice: Subject to any disclaimer, the term of this patent is extended or adjusted under 35 U.S.C. 154(b) by 0 days.

(21) Appl. No.: 13/514,695

(22) PCT Filed: Sep. 30, 2011

(86) PCT No.: PCT/KR2011/007250
§ 371 (c)(1),
(2), (4) Date: Jun. 8, 2012

(87) PCT Pub. No.: WO2012/070763
PCT Pub. Date: May 31, 2012

(65) Prior Publication Data
US 2012/0243656 A1     Sep. 27, 2012

(30) Foreign Application Priority Data
Nov. 25, 2010   (KR) .................. 10-2010-0118395

(51) Int. Cl.
*G01N 23/04*     (2006.01)

(52) U.S. Cl.
USPC ........................................................... 378/10

(58) Field of Classification Search ............... 378/4, 11, 378/10, 19, 51–55
See application file for complete search history.

(56) References Cited

U.S. PATENT DOCUMENTS

| | | | |
|---|---|---|---|
| 4,136,284 A * | 1/1979 | Blumental | 378/11 |
| 7,003,070 B1 * | 2/2006 | Chen et al. | 378/17 |
| 7,082,185 B2 | 7/2006 | Freifeld et al. | |
| 7,130,375 B1 | 10/2006 | Yun et al. | |
| 7,224,764 B2 | 5/2007 | Sukovic et al. | |
| 7,400,704 B1 | 7/2008 | Yun et al. | |
| 7,703,979 B2 * | 4/2010 | Chen et al. | 378/194 |
| 7,722,251 B2 | 5/2010 | Kang et al. | |
| 2004/0218716 A1 | 11/2004 | Freifeld et al. | |
| 2005/0053186 A1 | 3/2005 | Sukovic et al. | |
| 2009/0060129 A1 | 3/2009 | Kang et al. | |

FOREIGN PATENT DOCUMENTS

KR    10-2010-0087245 A    8/2010

* cited by examiner

*Primary Examiner* — Irakli Kiknadze
(74) *Attorney, Agent, or Firm* — Rabin & Berdo, P.C.

(57) ABSTRACT

A computed tomography apparatus for geological resource core analysis, more particularly to a computed tomography apparatus for geological resource core analysis in that it can conveniently utilize a computed tomography apparatus for industrial use, the movement between the CT beam transmitter and the detector is decreased, thereby performing an accurate measurement and breaking down infrequently, and especially, it can easily perform a CT scan on a cylinder type (or rod shape) sample having a very long major axis such as a geological resource core sample.

3 Claims, 8 Drawing Sheets

COMPUTED TOMOGRAPHY APPARATUS FOR GEOLOGICAL RESOURCE CORE ANALYSIS

TECHNICAL FIELD

The present invention relates to a computed tomography apparatus for geological resource core analysis, more particularly to a computed tomography apparatus for geological resource core analysis in that it can conveniently utilize a computed tomography apparatus for industrial use, the movement between the CT beam transmitter and the detector is decreased, thereby performing an accurate measurement and breaking down infrequently, and especially, it can easily perform a CT scan on a cylinder type (rod shape) sample having a very long major axis such as a geological resource core sample.

BACKGROUND ART

Figure 1:
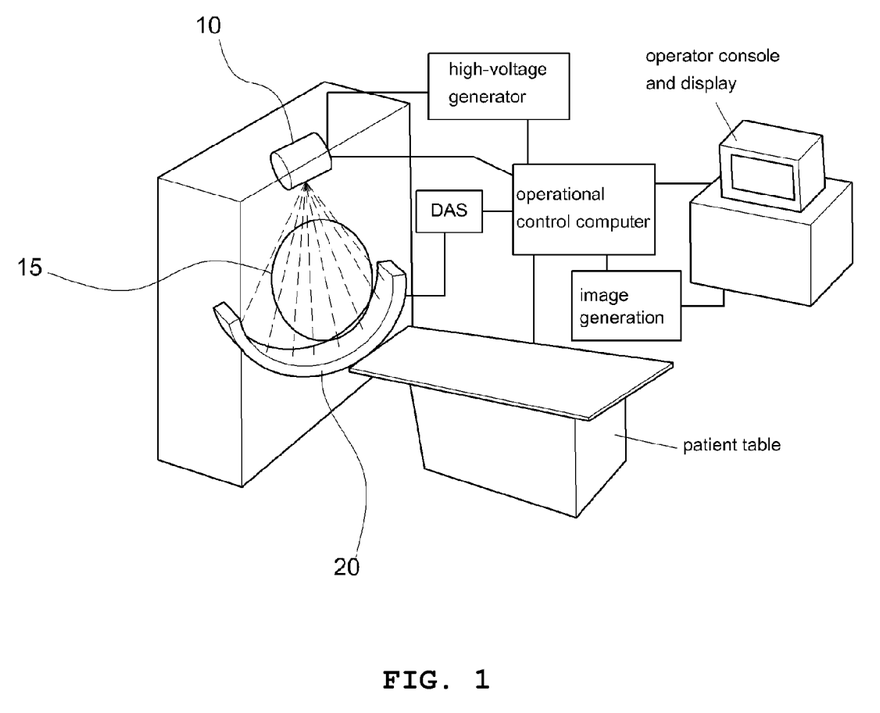
FIG. 1 is an example view illustrating a conventional computer tomography apparatus.

In general, a computer tomography apparatus (CT) for medical purposes has a construction shown in FIG. 1. The best feature of the CT for medical purpose is a circular ring called as a gantry 15. In the frame of the ring thereof, the CT beam transmission part 10 and the X-ray detector 20 are opposed to each other.

At this time, in the X-ray detector 20, the X-ray detecting elements are linearly arranged. The CT beam transmission part 10 transmits the X-ray of a fan beam shape toward only the linear elements of the X-ray detector 20.

Figure 2:
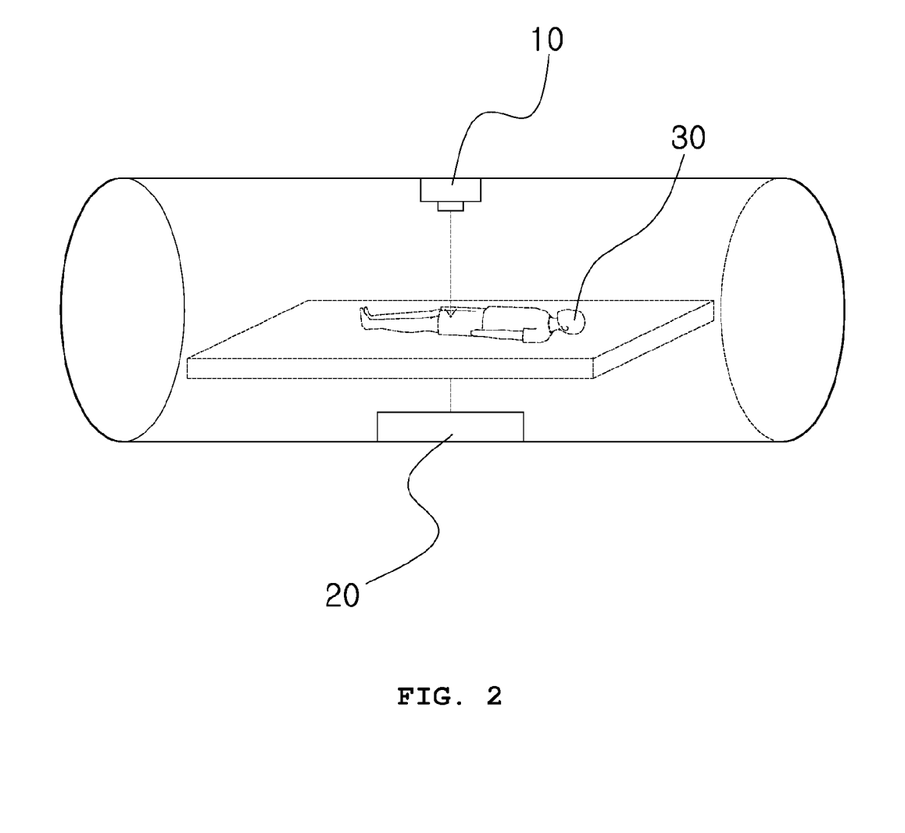
FIG. 2 and FIG. 3 are example views illustrating an example of left and right scan according to a conventional computer tomography apparatus.
Figure 3:
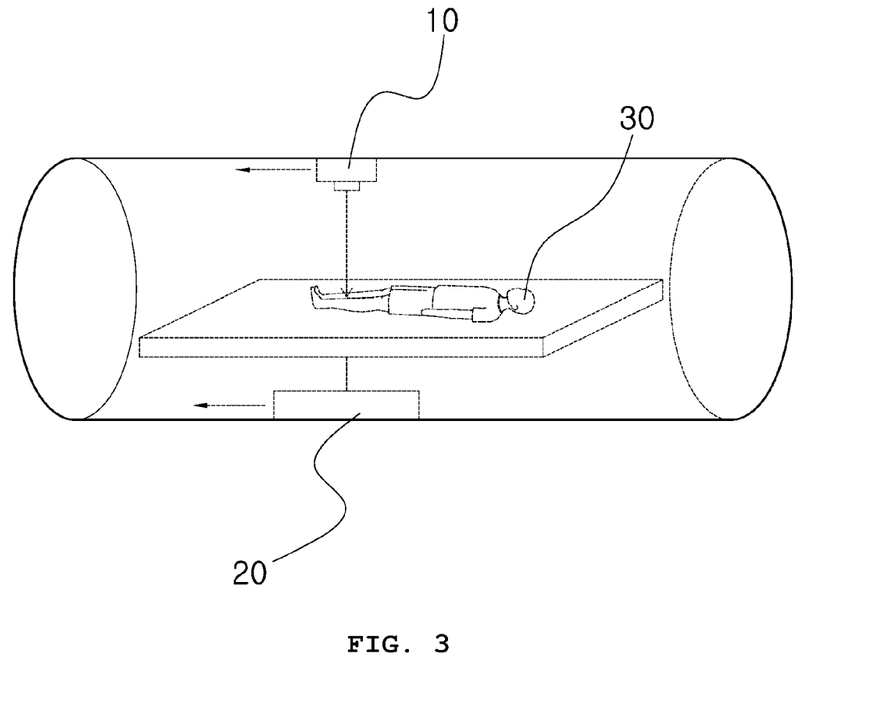
Figure 4:
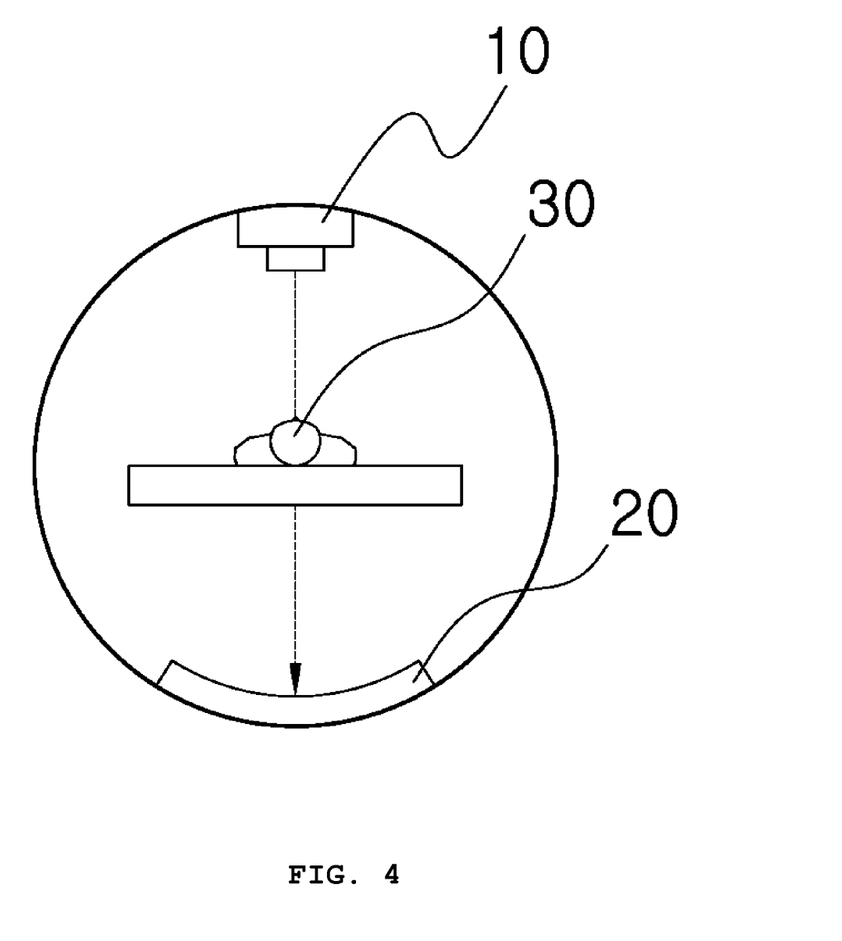
FIG. 4 and FIG. 5 are example views illustrating an example of up and down scan according to a conventional computer tomography apparatus.
Figure 5:
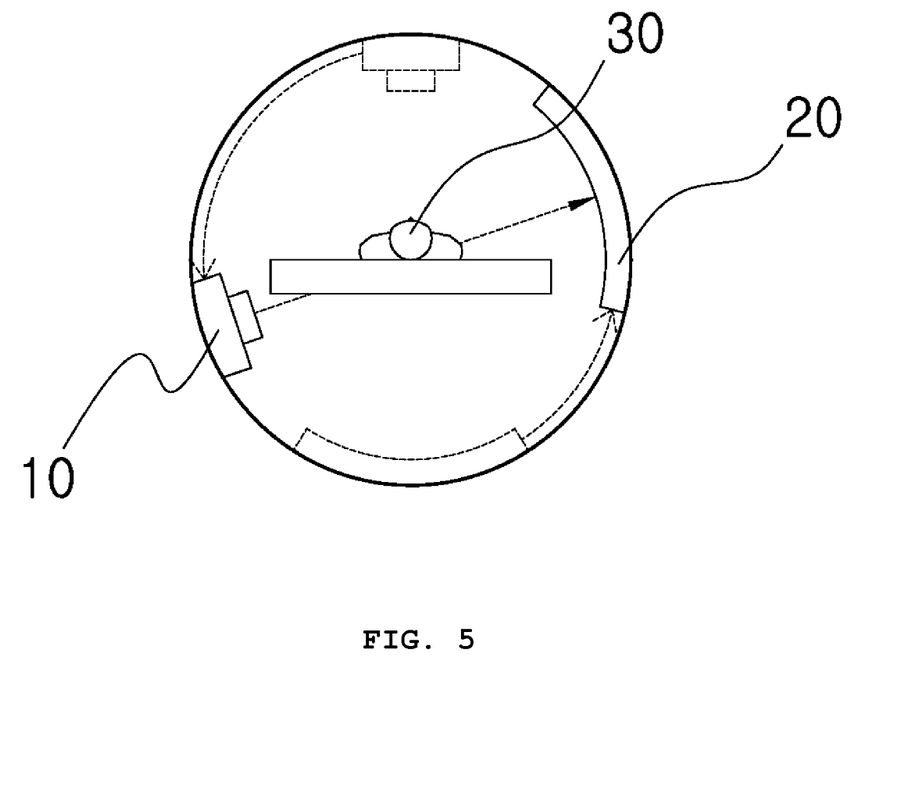

In order to do a computed tomography scan on a subject (patient), it is necessary to scan the subject at an angle of 360 degrees. As shown in FIG. 2 and FIG. 3, the CT beam transmission part 10 and the X-ray detector 20 are moved left and right to be scanned. Or, As shown in FIG. 4 and FIG. 5, the CT beam transmission part 10 and the X-ray detector 20 are rotated to be scanned.

Meanwhile, in the computer tomography apparatus (CT) for medical purposes using another method, it rotates the gantry, so that the subject (patient) can be continually scanned.

Also, it is necessary to longitudinally scan the subject (patient) at an angle of 360 degrees. In order to solve this demand, the bed, on which the patient is lying, is horizontally moved parallel to the rotation axis thereof in the inside of the gantry, which is under a continuous rotation scanning.

The scanning methods are already well-known in the prior art. In these scanning methods, the X-ray detecting elements are linearly arranged on the detector and the X-ray of the fan beam shape is irradiated. At this time, it scans the patient in the direction of the axis of ordinates, so that the radiation exposure on the patient can be minimized.

In the meantime, in order to prevent the scan result from being deteriorated owing to the unconscious movement of the patient during the scanning, it is necessary to scan the patient as soon as possible.

In this case, it is necessary to rotate the gantry having a significant weight as soon as possible and minimize the irregular vibration of the gantry. Accordingly, the cost of constructing the hardware for satisfying these requirements is considerable.

In the meantime, the industrial computer tomography apparatus does not need parts of the technical requirements, which is required in the medical computer tomography apparatus.

That is, in case of inanimate subjects, there is no need to minimize the radiation exposure and complete the scan in the least amount of time. That is, it is not necessary to rotate the CT beam transmission part and the X-ray detector to high speeds through the gantry like the medical CT. In some cases, the CT beam transmission part and the X-ray detector are rather fixed and the subject is rotated at an angle of 360 to be scanned.

Like this, the gantry or the subject are rotated to low speeds, so that the irregular vibration can be decreased, thereby more improving the resolution of the computer tomography.

That is, the industrial CT can obtain a better result thereof at a low cost in comparison with the medical CT.

In industry, since the articles of requiring the X-ray CT are very various, the industrial X-ray CT is often customized in consideration of the characteristic of the subject. Mainly, the formats of each part thereof are divided into several kinds in consideration of the shape and size of the subject.

Firstly, in the most common manner, the CT beam transmission part and the X-ray detector are fixed to both ends thereof and the rotation axis is linearly arranged between them. At this time, the subject located on the rotation axis is rotated at an angle of 360 degrees to be scanned.

Large numbers of the computer tomography apparatuses for scanning the general industrial products such as a tire or an electronic substrate belong to this shape.

In some cases, the rotation axis located between the CT beam transmission part and the X-ray detector can be manufactured in the variable type so as to be moved along any one of three linear axes.

For special example, in the dental CT, the CT beam transmission part and the X-ray detector include a pair of gantries, so that they rotate the surroundings of the head of the patient at an angle of 360 degrees to be scanned.

In case of the general CT for medical purpose, since it rotates the surroundings of the head of the patient sitting, the rotation axis is located on the upper part of the patient's head and it horizontally rotates the surroundings of the head of the patient.

That is, the gantries of the general medical CT and the dental CT form an angle of 45 degrees. However, the rotation directions thereof are different from each other.

In rare cases, the subject is fixed thereto or horizontally moved and the gantry rotates the surroundings of the subject.

In this case, as described above, the resolution thereof can be deteriorated owing to the vibration phenomenon of the gantry.

In the field of the geological resource, the X-ray scan is typically conducted so as to grasp the physical properties of the drilling core obtained by the stratum drilling.

Since the shape of the drilling core is a cylinder, where the X-ray scan is simply performed with the object of viewing the interior structure thereof, it is not easy to grasp the physical properties inside the core owing to very different X-ray transmission images between the middle and edge portions thereof.

In order to overcome the problem in the field of the geological resource, a thin slab (piece type) sample is again collected from the geological sample to be X-ray scanned.

However, in case of collecting the sample in addition, it is time-consuming. Also, in case of any core sample obtained from soft stratum, it is not easy to collect the piece type sample itself.

In order to solve this problem, the research organization of the geological resource all over the world had been tried to scan the core itself through the computer tomography apparatus. However, the optimization CT on the sample core of the cylinder shape is not yet developed. That is, it remains an unsolved problem.

In other word, since the cylinder type sample has a very long major axis, it cannot smoothly perform the experiment required in the field of the geological resource by using the CT beam transmission part and the X-ray detector and by means of the arranging and operating manners of the rotation axis used in the existed industrial CT.

In order to solve this problem, it has been tried to scan the core itself through the medical computer tomography apparatus. However, the core sample requires more sufficient X-ray san than that of the medical CT. Accordingly, it cannot also, smoothly perform the experiment required in the field of the geological resource.

Meanwhile, in the field of the geological resource, a very small fragment or a very small mini core of a cylinder shape are again collected from the core sample to be CT-scanned.

At this time, in order to observe the minute physical properties of the core such as a microcrack or a particle array pattern etc. under high resolution, it often utilizes the method of the geometric magnification.

Generally, since the size of the detector is limited, where the size of the subject is small, it is easier to geometrically magnify the subject.

In order to focus the maximum image inside the detector, it is necessary to perform the CT scan with the rotation axis near the CT beam transmission part as possible.

When it treats the considerable small samples, since the CT beam can sufficiently penetrate the samples by means of only a small X-ray power, the CT beam transmission part having a small voltage capacity and a high resolution is utilized. Accordingly, in accordance with this structure, there is a general trend of manufacturing and using the micro X-ray CT separately.

The CT apparatuses generate the radiation without exception. Accordingly, to shield the X-ray properly is a main task for the CT fabrication.

In case of the medical CT, as described above, it is constructed in such a manner that the radiation exposure of the patient can be minimized and then, the radiation is emitted on the patient without separate shielding. In the meantime, in order to shield the radiation on the workers of the CT control room etc., the outside of the scanning room is shielded from the radiation, so that it can prevent the radiation from penetrating the CT control room etc.

However, In case of the industrial CT, since it has any voltage much higher than the medical CT and emits the radiation longer than the medical CT, the sufficient shielding device should be prepared at any cost.

In the most common shielding manner, it constructs a cabinet type shielding device, so that the entire CT including the CT beam transmission part, the X-ray detector and the rotation axis between them is surrounded by a lead plate etc. to be shielded.

That is, the CT includes the shielding device located on the outside thereof.

However, in this case, since the entire space thereof is restricted by the size of the cabinet, the size of the analyzing sample is restricted without question.

Accordingly, it is necessary to suggest an alternative, instead of the cabinet type shielding device. Also, it seeks to properly control the surrounding conditions such as a temperature and a humidity etc. suitable for the condition of the experimental sample.

Recently, in the field of the geological resource, it spurs the exploration and development of the special sample called as a gas hydrate, thereby the demand on the CT scan has been remarkably increased.

The gas hydrate is spread in the deep seafloor or subsurface thereof. The hydrate is existed in the form of an ice owing to the low-temperature and high-pressure condition provided by the surroundings thereof. Also, it contains much marsh gas therein.

Since the gas hydrate is dissociated in a state of nature to be dissipated, the sample should be stored in an extremely low temperature or pressure vessel having a hard pressure so as to protect it in good condition. At this time, the latter is widely used, because it is closer to the state of nature.

The gas hydrate is collected together with the stratum drilling. Accordingly, the cylinder type core, that is, the core sample is composed of the gas hydrate along with the perimetrical sediment.

Accordingly, the container of filling the gas hydrate is a cylinder type and made of a metal component capable of handling the pressure well.

Since it cannot take out and observe the sample from the opaque container, the CT scan manner is experimentally applied thereto. The material of the container is an X-ray permeable metal such as an aluminum.

Also, as though the gas hydrate is contained in the metal container, where the gas hydrate is completely dissociated, it can explode. Moreover, it keeps the gas hydrate pressure refrigerated in a temperature of 4° all the time.

That is, in the CT experiment on the gas hydrate sample, to maintain the temperature condition of about 4° around the CT apparatus is the key to success. However, it is very difficult for the existed cabinet type shielding CT to meet this condition.

If a refrigerator is installed in the inside of the small cabinet type shielding membrane, since the vibration generated by the operation of the refrigerator is directly transmitted to the CT parts, it is hard to obtain the high resolution material.

Accordingly, where the gas hydrate sample is presently scanned through the CT apparatus in the field of the geological resource, the research teams all over the world have been searched for the optimum plan as to whether the special facility for controlling the temperature and humidity around the CT is combined with the CT apparatus or not.

Also, a big cylinder capable of covering the subject is required. Moreover, it is necessary to make any device capable of rotating the CT beam transmission part and the detector or moving them left and right at the same time. Accordingly, the manufacturing cost thereof becomes more expensive. Since the CT beam transmission part and the detector are rotated or moved left and right, it is frequently out of work, thereby increasing the maintenance cost. Also, since the operations of rotating or horizontally moving the CT beam transmitter and the detector are large, it is out of focus, thereby it has difficulty in performing the accurate measurement.

Accordingly, it has considerable difficulty for using as the industrial CT, besides the medical CT. An improvement thereof has been remained a big issue in the art.

DISCLOSURE

Technical Problem

Therefore, the present invention has been made in view of the above-mentioned problems, and an object of the present invention is to provide a computed tomography apparatus for geological resource core analysis capable of effectively performing a CT scan on a cylinder type sample having a very long major axis or a similar rod shape sample.

Another object of the present invention is to provide a computed tomography apparatus for geological resource core analysis capable of performing an accurate measurement by reducing the movement between the CT beam transmitter and the detector.

Further another object of the present invention is to provide a computed tomography apparatus for geological resource core analysis in that it is not frequently out of work, thereby reducing the repair cost.

Further another object of the present invention is to provide a computed tomography apparatus for geological resource core analysis in that it improves a problem that the entire sample cannot be scanned by a single tomography, where the sample is a cylinder shape and the length of the major axis of the sample is larger than that of the surface of the detector, so that the sample of the cylinder type can be partially scanned, thereby conduct the proper computed tomography of the sample.

Further another object of the present invention is to provide a computed tomography apparatus for geological resource core analysis in that the CT scan having the resolution of a micrometer scale can be performed on a big sample as well as a small sample (cubic centimeter or cubic millimeter), which are collected from the existed sample.

Further another object of the present invention is to provide a computed tomography apparatus for geological resource core analysis in that a main body and first and second supporting members are made of a heatproof, a wetproof, and a shock-resistant rock, so that it eliminates the vibration phenomenon, thereby increasing the accuracy thereof.

Technical Solution

In accordance with the present invention to achieve the object thereof, there is provided a computed tomography apparatus for geological resource core analysis in that a CT beam transmitter and a detector are not rotated or not moved left and right, a sample (subject) thereof is rotated, and the CT beam transmission part and the detector are simultaneously moved up and down by transmitting an operation signal, which is synchronized with the operation signal of the CT beam transmission part operating motor, to a detector operating motor.

Accordingly, the movement between the CT beam transmitter and the detector is decreased, thereby performing an accurate measurement and breaking down infrequently.

Advantageous Effects

According to the computed tomography apparatus for geological resource core analysis, there are effects in that it can conveniently utilize a computed tomography apparatus for industrial use and the movement between the CT beam transmitter and the detector is decreased, thereby performing the accurate measurement thereof.

Also, there is another effect in that the computed tomography apparatus is not frequently out of work, thereby reducing the repair cost.

According to the present invention, the cylinder type sample having a very long major axis can be scanned through the computed tomography apparatus without meeting any obstruction and the sample can be restored in three dimensions. Also, when the CT beam transmission part, the sample locate at the rotation axis, and the X-ray detector are appropriately and spatially arranged according to the geometric magnification required, if the cylinder type sample has a very long major axis, only a part of the sample can be created as an image through the detector. At this time, firstly, the part of the sample is scanned and then, the rest of the sample is scanned by moving the CT beam transmission part and the detector upwardly or downwardly, thereby solving the corresponding problem. Moreover, as though the cylinder type sample has a very long major axis, the CT scan is repeated a several times and the results are accumulated, thereby solving the problem.

Also, the sample of a big size can be comfortably scanned and the CT scan having the resolution of a micrometer scale can be performed in case of the sample of a suitable size.

Moreover, since the sample rotating device and the supporting members having the X-ray detector can be moved horizontally, the distance between the CT beam transmission part and the detector and the distance between the sample and the detector can be automatically adjusted respectively, so that the distance between the CT beam transmission part and the detector is minimized and the distance between the sample and the detector is maximized, thereby obtaining the maximum geometric magnification.

Moreover, a pressure core sample of a gas hydrate type, which is very difficult test subject in the field of the geological resource, can be safely scanned.

BRIEF DESCRIPTION OF THE DRAWINGS

The foregoing and other objects, features and advantages of the present invention will become more apparent from the following detailed description when taken in conjunction with the accompanying drawings in which.

DESCRIPTIONS ON REFERENCE NUMBERS FOR THE MAJOR COMPONENTS IN THE DRAWINGS

100: CT beam transmission part
110: CT beam transmission part moving member
200: detector
210: detector moving member
300: sample
310: sample rotating device
410: CT beam transmission part operating motor
420: sample rotating motor
430: detector operating motor
500: monitoring system
510: operating part
520: motor controller
530: display part
540: central controller
700: main body
710: first supporting member
720: second supporting member

BEST MODE

Mode for Invention

In accordance with the present invention to achieve the object thereof, there is provided a computed tomography apparatus for geological resource core analysis including:

a main body 700 having a CT beam transmission part 100, a detector 200, and a sample rotating device 310;

the CT beam transmission part 100 installed and constructed in a first supporting member 710 installed in one side of the main body, connected to a CT beam transmission part moving member 110, moved up and down when the CT beam transmission part moving member is moved up and down, and transmitting a CT beam;

the detector 200 installed and constructed in a second supporting member 720 installed in the other side of the main body, connected to a detector moving member 210, moved up and down though the detector moving member 210, and acquiring the CT beam transmitted through the CT beam transmission part 100; and the sample rotating device 310 installed and constructed between the CT beam transmission part 100 and the detector 200 and fixing a sample 300 to be rotated.

In the meantime, a computed tomography apparatus for geological resource core analysis according to another embodiment of the present invention includes:

a main body 700 having a CT beam transmission part 100, a detector 200, and a sample rotating device 310;

the CT beam transmission part 100 installed and constructed in a first supporting member 710 installed in one side of the main body, connected to a CT beam transmission part moving member 110, moved up and down when the CT beam transmission part moving member is moved up and down, and transmitting a CT beam;

the detector 200 installed and constructed in a second supporting member 720 installed in the other side of the main body, connected to a detector moving member 210, moved up and down though the detector moving member 210, and acquiring the CT beam transmitted through the CT beam transmission part 100;

the sample rotating device 310 installed and constructed between the CT beam transmission part 100 and the detector 200 and fixing a sample 300 to be rotated;

a CT beam transmission part operating motor 410 for moving the CT beam transmission part moving member 110 up and down;

a detector operating motor 430 for moving the detector moving member 210 up and down; and a sample rotating motor 420 for rotating the sample rotating device.

In the meantime, a computed tomography apparatus for geological resource core analysis according to further another embodiment of the present invention includes:

a main body 700 having a CT beam transmission part 100, a detector 200, and a sample rotating device 310;

the CT beam transmission part 100 installed and constructed in a first supporting member 710 installed in one side of the main body, connected to a CT beam transmission part moving member 110, moved up and down when the CT beam transmission part moving member is moved up and down, and transmitting a CT beam;

the detector 200 installed and constructed in a second supporting member 720 installed in the other side of the main body, connected to a detector moving member 210, moved up and down though the detector moving member 210, and acquiring the CT beam transmitted through the CT beam transmission part 100;

the sample rotating device 310 installed and constructed between the CT beam transmission part 100 and the detector 200 and fixing a sample 300 to be rotated;

a CT beam transmission part operating motor 410 for moving the CT beam transmission part moving member 110 up and down;

a detector operating motor 430 for moving the detector moving member 210 up and down;

a sample rotating motor 420 for rotating the sample rotating device; and a central controller 540 for transmitting operation signals to the CT beam transmission part operating motor 410, the detector operating motor 430 and the sample rotating motor 420, transmitting a CT beam transmission signal to the CT beam transmission part 100, and allowing the CT beam transmission part 100 and the detector 200 to be simultaneously moved up and down by transmitting an operation signal, which is synchronized with the operation signal of the CT beam transmission part operating motor 410, to the detector operating motor 430.

Here, the computed tomography apparatus for geological resource core analysis according to further another embodiment of the present invention further includes a motor controller 520 for receiving the operation signals from the central controller thereby operating the CT beam transmission part operating motor, the detector operating motor, and the sample rotating motor.

In the meantime, the computed tomography apparatus for geological resource core analysis according to additional aspect of the present invention further includes an operating part 510 for moving the CT beam transmission part 100 and the detector 200 up and down, rotating the sample rotating device 310, and allowing the operation of transmitting the CT beam to be selected by an user; and a display part 530 for displaying the data detected by the detector 200.

Also, the computed tomography apparatus for geological resource core analysis according to additional aspect of the present invention further includes a driving motor of the sample rotating device for moving the sample rotating device left and right.

Here, the main body and the first and second supporting members are made of a heatproof, a wetproof, and a shock-resistant rock, so that it eliminates the vibration phenomenon, thereby increasing an accuracy thereof.

Hereinafter, exemplary embodiments of the present invention will be described in detail with reference to the accompanying drawings.

Figure 6:
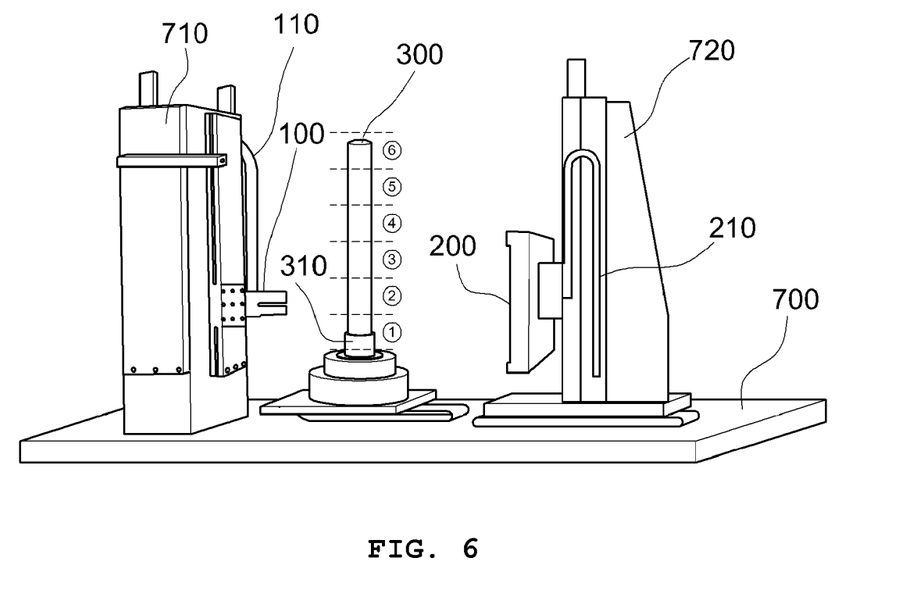
FIG. 6 is a constructional view illustrating a computed tomography apparatus for geological resource core analysis according to one embodiment of the present invention.

FIG. 6 is a constructional view illustrating a computed tomography apparatus for geological resource core analysis according to one embodiment of the present invention.

Figure 7:
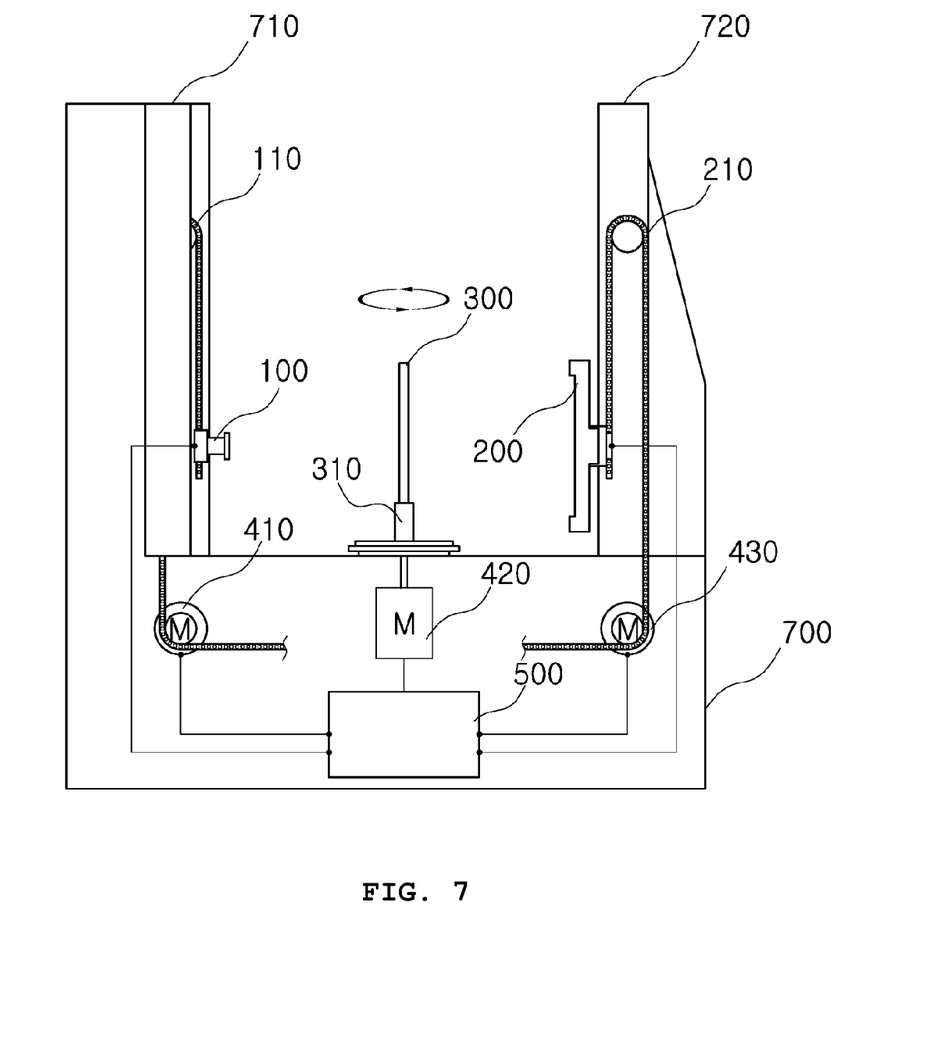
FIG. 7 is a sectional view illustrating a computed tomography apparatus for geological resource core analysis according to one embodiment of the present invention.

FIG. 7 is a sectional view illustrating a computed tomography apparatus for geological resource core analysis according to one embodiment of the present invention.

As shown in FIG. 6 and FIG. 7, the computed tomography apparatus for geological resource core analysis according to one embodiment of the present invention includes a main body 700 having a CT beam transmission part 100, a detector 200, and a sample rotating device 310;

the CT beam transmission part 100 installed and constructed in a first supporting member 710 installed in one side of the main body, connected to a CT beam transmission part moving member 110, moved up and down when the CT beam transmission part moving member is moved up and down, and transmitting a CT beam;

the detector 200 installed and constructed in a second supporting member 720 installed in the other side of the main body, connected to a detector moving member 210, moved up and down though the detector moving member 210, and acquiring the CT beam transmitted through the CT beam transmission part 100; and the sample rotating device 310 installed and constructed between the CT beam transmission part 100 and the detector 200 and fixing a sample 300 to be rotated.

The main body and the first and second supporting members are made of a heatproof, a wetproof, and a shock-resistant rock, so that it eliminates the vibration phenomenon, thereby increasing the accuracy thereof.

The sample rotating device for rotating the subject (sample) at an angle of 360 degrees is formed between the CT beam transmission part 100 and the detector 200.

Also, the computed tomography apparatus for geological resource core analysis according to one embodiment of the present invention further includes a driving motor (not shown) of the sample rotating device so as to move the sample rotating device left and right.

Accordingly, since the sample rotating device 310 and the second supporting member 720 having the detector 200 can be moved horizontally (left and right), the distance between the CT beam transmission part 100 and the detector 200 and the distance between the sample 300 and the detector 200 can be automatically adjusted respectively, so that the distance between the CT beam transmission part 100 and the detector 200 is minimized and the distance between the sample 300 and the detector 200 is maximized, thereby obtaining the maximum geometric magnification.

Also, since a moving member capable of moving by means of the driving motor of the sample rotating device is provided therein, when the driving motor of the sample rotating device is operated, the moving member is moved left and right.

That is, in order to increase the resolution thereof more and more, where the detector 200 is moved, the sample rotating device 310 is moved as necessary. At this time, they can move together or inversely.

For example, when the sample is small, the sample rotating device 310 should place near the CT beam transmission part 100 so as to obtain the image of high resolution. On the contrary, when the sample is big, the sample rotating device 310 should be away from the CT beam transmission part 100, so that it can obtain the image of high resolution.

Also, in order to obtain the safety thereof on the change of room temperature, the change of humidity, and the vibration and so on, the main body 700 and the first and second supporting members 710 and 720 are made of a heatproof, a wetproof, and a shock-resistant material such as the rock etc.

Here, the CT beam transmission part 100 should emit a cone-beam, not a fan beam. Also, the detector 200 utilizes a planar detector.

In the conventional computer tomography apparatus (CT) for medical purposes of laying the subject thereon and a similar industrial CT, they cannot receive a big sample, so long as it is built on a large scale. However, in the present invention, as though the sample has a major axis of a meter-long, if the height of the ceiling thereof is appropriately adjusted in the external shielding device, it can accommodate any amount of the sample.

The CT beam transmission part 100 and the detector 200, which are opposed to each other around the sample rotating device 310 between them, should be formed at the side support of a pillar shape. Also, the above elements are moved up and down along the moving member formed on the support member by means of the electric driving manner.

At this time, The CT beam transmission part 100 and the detector 200 can be moved up and down together or separately according to the choice of the driver.

Also, two moving members are formed on front and side surfaces of the first supporting member 710 having the CT beam transmission part 100 respectively, so that two type of CT beam transmission parts such as a voltage-capacity type, an X-ray emitting type and so on can be attached to each moving member, thereby widening the limit of application thereof.

That is, it means that the CT beam transmission part can be additionally attached thereto so as to increase the resolution thereof.

In case of the sample rotating device 310 installed between the CT beam transmission part and detector and formed at the upper portion of the main body, the moving member is formed at the lower portion of the rotational axis thereof and it can be moved horizontally between the CT beam transmission part and detector through the electric adjustment.

Also, in case of the second supporting member 720 having the detector 200, the moving member is formed thereon and it can be moved horizontally through the electric adjustment.

Accordingly, the distance between the CT beam transmission part 100 and the detector 200 and the distance between the sample 300 and the detector 200 can be automatically adjusted, thereby obtaining the maximum geometric magnification as necessary.

Here, if the locations of the CT beam transmission part 100 and the detector 200 are completely fixed and the location of the sample rotating device, that is, only the location of the sample is changed, there are limits on the geometric magnification or the choice of the sample size. However, in order to overcome it, the CT of the present invention is provided with not only the sample rotating device but the horizontal moving means of the detector.

In the meantime, wide discs are arranged on the sample rotating device 310 and grooves are appropriately formed at each disc, so that it can widely accommodate various jigs.

The various jigs are appropriately manufactured according to the shape of the samples, which are objects of the computed tomography and serve as a support of the sample.

Especially, in order to accommodate the cylinder type sample having a very long major axis on the direct upper portion of the sample rotating device 310, the shielding device of a cabinet type is not installed.

Instead of the shielding device of a cabinet type, it can shield the entire room having the computed tomography, so that the vertical length of the sample can reach the height of the ceiling of the laboratory. Moreover, in order to perform the computed tomography on the special sample, which is in want of a low temperature condition or a constant humidity condition, separate cooling device and constant humidity device can be formed in the laboratory.

In the meantime, where the sample is a cylinder shape and the length of the major axis of the sample is larger than that of the surface of the detector, there is a problem in that the entire sample cannot be scanned by a single tomography. Accordingly, in order to improve the problem, the sample of the cylinder type can be partially scanned, thereby conduct the proper computed tomography of the sample.

For example, as shown in FIG. 6, the first area is scanned, the second area is scanned, the third area is scanned, the fourth area is scanned, the fifth area is scanned, the sixth area is scanned, and then, finally the total scanned areas of 1-6 are combined into one image through a central controller or an image treating part. Here, since the technique for combining each image into one image is already well-known in the art, concrete descriptions on this are omitted here.

That is, where the first area through the sixth area are scanned at a time, the resolution thereof is deteriorate. Accordingly, the scanning areas are designated and then, the detector and the CT beam transmission part are horizontally moved toward the corresponding area to scan them, thereby increasing the resolution thereof up to a square of the partial area.

For example, if it is partially scanned in six areas, the resolution thereof is $6^2$. Accordingly, the resolution thereof can be increased up to 36 times to the max in comparison with one tomography thereof.

Also, in order to concretely analyze the sample, the partial tomography can be conducted.

In the meantime, the computed tomography apparatus for geological resource core analysis according to one embodiment of the present invention can further include a monitoring system 500 for monitoring the vertical movement of the CT beam transmission part and the detector, the rotation operation of the sample, the transmitting signal of the CT beam, and the detected data of the detector and so on. Accordingly, the user can easily check out the operation thereof and the detected data through the monitoring system 500.

The CT beam transmission part 100 is installed and constructed in a first supporting member 710 installed in one side of the main body 700 of the present invention. Also, the CT beam transmission part is connected to the CT beam transmission part moving member 110, so that it is moved up and down when the moving member of the CT beam transmission part is moved up and down.

Also, the central controller 540 serves to obtain a CT beam transmission signal during the transmission of CT beam transmission signal, scan the CT beam on the sample (subject), and output the detected signal, which is detected from the detector 200 via the sample, to the user.

The detector 200 is installed in the second supporting member 720 installed in the other side of the main body of the present invention. The detector 200 is connected to the detector moving member 210. Especially, the detector 200 is synchronized with the CT beam transmission part 100, so that it is moved up and down through the detector moving member 210 during the movement of the detector moving member 210. Also, the detector acquires the CT beam transmitted through the CT beam transmission part.

Here, according to the synchronization thereof, if the CT beam transmission part is moved up, the detector is also moved up. On the contrary, if the CT beam transmission part is moved down, the detector is also moved down.

The sample 300 is located between the CT beam transmission part and the detector to be rotated.

In the conventional art, the CT beam transmission part and the detector are rotated. However, as described above, in the present invention, the sample that is, the subject are rotated.

Accordingly, it can be provided to perform an accurate measurement by reducing the movement between the CT beam transmitter and the detector. Also, since the movement between the CT beam transmitter and the detector can be decreased, there is a merit in that it breaks down infrequently.

At this time, the sample is fixed to a sample fixing part (not shown) and then, it prevents the sample from being deviated from the sample fixing part during the rotation thereof through the motor.

Here, the sample is rotated, so that it can obtain the images detected at various angles so as to analyze the materials existed in the sample, thereby minutely measuring it more and more.

Figure 8:
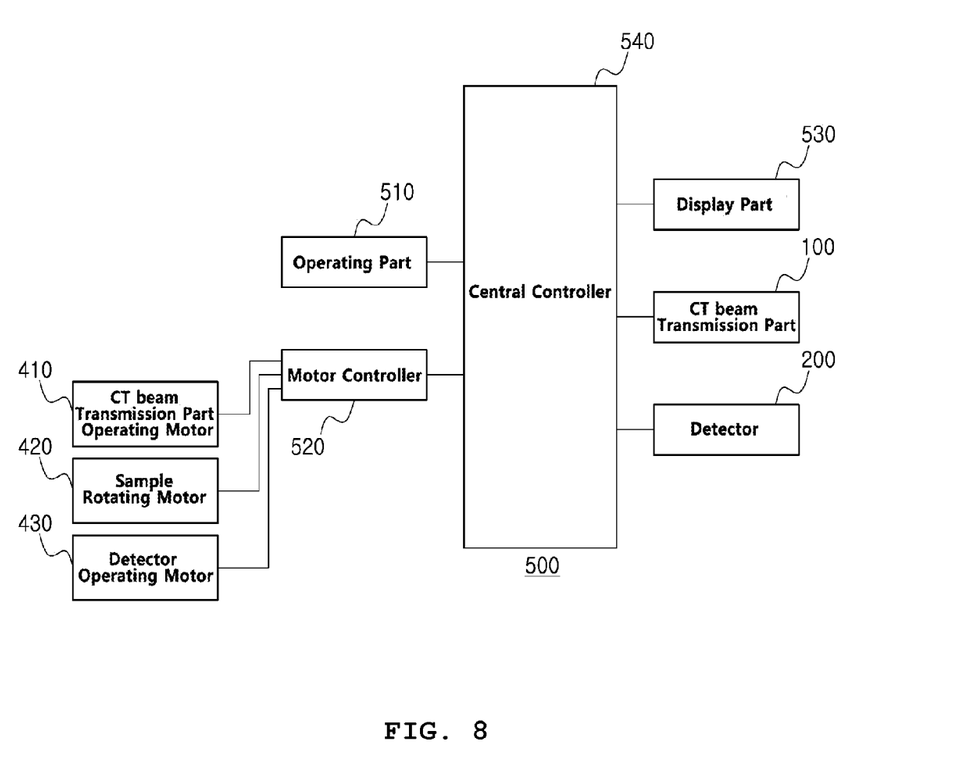
FIG. 8 is a block diagram illustrating a computed tomography apparatus for geological resource core analysis according to one embodiment of the present invention.

FIG. 8 is a block diagram illustrating a computed tomography apparatus for geological resource core analysis according to one embodiment of the present invention.

As shown in FIG. 8, the computed tomography apparatus for geological resource core analysis according to one embodiment of the present invention includes a main body 700 having a CT beam transmission part 100, a detector 200, and a sample rotating device 310;

the CT beam transmission part 100 installed and constructed in a first supporting member 710 installed in one side of the main body, connected to a CT beam transmission part moving member 110, moved up and down when the CT beam transmission part moving member 110 is moved up and down, and transmitting a CT beam;

the detector 200 installed and constructed in a second supporting member 720 installed in the other side of the main body, connected to a detector moving member 210, moved up and down though the detector moving member 210, and acquiring the CT beam transmitted through the CT beam transmission part 100;

the sample rotating device 310 installed and constructed between the CT beam transmission part 100 and the detector 200 and fixing a sample 300 to be rotated;

a CT beam transmission part operating motor 410 for moving the CT beam transmission part moving member 110 up and down;

a detector operating motor 430 for moving the detector moving member 210 up and down;

a sample rotating motor 420 for rotating the sample 300;

a central controller 540 for transmitting operation signals to the CT beam transmission part operating motor 410, the detector operating motor 430 and the sample rotating motor 420, transmitting a CT beam transmission signal to the CT beam transmission part 100, and allowing the CT beam transmission part 100 and the detector 200 to be simultaneously moved up and down by transmitting an operation signal, which is synchronized with the operation signal of the CT beam transmission part operating motor 410, to the detector operating motor 430;

a motor controller 520 for receiving the operation signals from the central controller 540 thereby operating the CT beam transmission part operating motor 410, the detector operating motor 430, and the sample rotating motor 420;

an operating part 510 for moving the CT beam transmission part 100 and the detector 200 up and down, rotating the sample rotating device 310, and allowing the operation of transmitting the CT beam to be selected by the user; and a display part 530 for displaying the data detected by the detector 200.

In the present invention, it needs a driving means for moving the CT beam transmission part 100 and the detector 200 up and down and rotating the sample 300. Preferably, the driving means is a motor.

That is, the driving means includes the CT beam transmission part operating motor 410 for moving the CT beam transmission part moving member 110 up and down, the detector operating motor 430 for moving the detector moving member 210 up and down, and the sample rotating motor 420 for rotating the sample 300.

The CT beam transmission part operating motor 410 serves to move the CT beam transmission part moving member 110 up and down. That is, the CT beam transmission part moving member 110 is moved up and down by means of the operation of the motor.

The detector operating motor 430 serves to move the detector moving member 210 up and down. That is, the detector moving member 210 is moved up and down by means of the operation of the motor.

The sample rotating motor 420 serves to rotate the sample 300.

At this time, the central controller 540 serves to transmit the operation signals to the CT beam transmission part operating motor 410, the detector operating motor 430 and the sample rotating motor 420.

Also, according to additional embodiment of the present invention, the computed tomography apparatus for geological resource core analysis further includes a driving motor of the sample rotating device for moving the sample rotating device left and right. In this case, the central controller transmits the operation signal to the driving motor of the sample rotating device so as to move the sample rotating device.

If the user operates the operating part 510 so as to move the CT beam transmission part 100 up and down, the central controller 540 transmits the operation signal thereof to the CT beam transmission part operating motor 410 through the motor controller 520, thereby operating the CT beam transmission part operating motor 410.

At this time, the central controller 540 transmits any operation signal, which is synchronized with the operation signal of the CT beam transmission part operating motor 410, to the detector operating motor 430, to the motor controller 520 and then, the motor controller 520 transmits the operation signal to the detector operating motor 3G, thereby simultaneously moving the CT beam transmission part 100 and the detector 200 up and down.

The operating part 510 serves to move the CT beam transmission part 100 and the detector 200 up and down or rotate the sample 300. Also, it allows the operation of transmitting the CT beam to be selected by the user. Here, the operating part 510 may be an operational program or an operational button for user. The central controller 540 receives the signal operated by the user through the operating part 51, thereby performing the operation corresponding to the operation signal thereof.

Since the data processing techniques of the detector 200 and the operation thereof are already well-known in the art, further descriptions on these are omitted here.

According to the present invention, the cylinder type sample having a very long major axis can be scanned through the computed tomography apparatus without meeting any obstruction and the sample can be restored in three dimensions.

The technique for three dimensional restoration is already well-known in the art, further description on this is omitted here.

When the CT beam transmission part 100, the sample 300, and the detector 200 are appropriately and spatially arranged according to the geometric magnification required, if the cylinder type sample has a very long major axis, only a part of the sample can be created as an image through the detector. At this time, firstly, the part of the sample is scanned and then, the rest of the sample is scanned by moving the CT beam transmission part 100 and the detector 200 upwardly or downwardly, thereby solving the problem.

Accordingly, as though the cylinder type sample has a very long major axis, the CT scan is repeated a several times and the results are accumulated, thereby solving the problem.

By using a large planar detector, the sample can be scanned as large as possible during one CT scanning. Also, the size of the image can be exactly calculated at a time. Accordingly, there is no problem in that the CT scans are divided a several times and the scan data is accumulated.

In the present invention, the sample of a big size can be comfortably scanned. Also, in case of the sample of a suitable size, the CT scan having the resolution of a micrometer scale can be performed.

Accordingly, since the sample rotating device and the supporting members having the X-ray detector can be moved horizontally, the distance between the CT beam transmission part and the detector and the distance between the sample and the detector can be automatically adjusted respectively. That is, the distance between the CT beam transmission part and the detector is minimized and the distance between the sample and the detector is maximized, thereby obtaining the maximum geometric magnification.

Also, two moving members of the CT beam transmission part can be formed on the first supporting member having the CT beam transmission part. Also, since two CT beam transmission part can be installed thereon and two detectors can be separately attached thereto, as though the penetrating power thereof is very weak, the sample of a small size can be scanned at a maximum resolution through any one of two CT beam transmission part having a high resolution.

Also, a pressure core sample of a gas hydrate type, which is very difficult test subject in the field of the geological resource, can be safely scanned.

For example, the pressure core of a big size is partially divided to be scanned as described above, so that it can solve the problem owing to the big scale of the pressure core.

Also, since the entire room of the laboratory is shielded and the cooling device is formed on a proper space of the laboratory, the pressure core, which requires a cooling storage, can be scanned for long periods of time without any problems and the vibration, which is occurred by the operation of the cooling device, is not directly transmitted to the CT.

In the meantime, since the constant humidity device installed with the cooling device serves to maintain a constant humidity at a low temperature, it can prevent the dew condensation from being occurred at the peripheral portion of the CT parts owing to the frequent changes in humidity, thereby consistently driving the electric device.

By the structure of the laboratory, the device of the present invention can be effectively utilized more and more.

By means of the above construction and operation of the present invention, it can be easily utilized as an industrial computer tomography apparatus. Also, since the movement between the CT beam transmitter and the detector can be reduced, there is an effect in that it can be provided to perform the accurate measurement.

Also, since the computed tomography apparatus for geological resource core analysis according to the present invention is not frequently out of work, it can reduce the repair cost.

According to the present invention, the cylinder type sample having a very long major axis can be scanned through the computed tomography apparatus without meeting any obstruction and the sample can be restored in three dimensions. Also, when the CT beam transmission part, the sample locate at the rotation axis, and the X-ray detector are appropriately and spatially arranged according to the geometric magnification required, if the cylinder type sample has a very long major axis, only a part of the sample can be created as an image through the detector. At this time, firstly, the part of the sample is scanned and then, the rest of the sample is scanned by moving the CT beam transmission part 100 and the detector 200 upwardly or downwardly, thereby solving the problem. Moreover, as though the cylinder type sample has a very long major axis, the CT scan is repeated a several times and the results are accumulated, thereby solving the problem.

Although several exemplary embodiments of the present invention have been described for illustrative purposes, those skilled in the art will appreciate that various modifications, additions and substitutions are possible, without departing from the scope and spirit of the invention as disclosed in the accompanying claims.

INDUSTRIAL APPLICABILITY

The present invention relates to a computed tomography apparatus for geological resource core analysis, more particularly to a computed tomography apparatus for geological resource core analysis in that it can conveniently utilize a computed tomography apparatus for industrial use, the movement between the CT beam transmitter and the detector is decreased, thereby performing an accurate measurement and breaking down infrequently, and especially, it can easily perform a CT scan on a cylinder type (rod shape) sample having a very long major axis such as a geological resource core sample, whereby making good use of it in the field of the geological resource core analysis.

What is claimed is:

1. A computed tomography apparatus for geological resource core analysis, the computed tomography apparatus comprising:
   a main body supporting a first supporting member installed on one side thereof and a second supporting member installed on the other side thereof;
   a CT beam transmission part installed and constructed in the first supporting member, connected to a CT beam transmission part moving member, moved up and down by the CT beam transmission part moving member, and transmitting a CT beam;
   a detector installed and constructed in the second supporting member, connected to a detector moving member, moved up and down by the detector moving member, and acquiring the CT beam transmitted from the CT beam transmission part;
   a sample rotating device installed and constructed between the CT beam transmission part and the detector and fixing a sample to be rotated;
   a CT beam transmission part operating motor for moving the CT beam transmission part moving member up and down;
   a detector operating motor for moving the detector moving member up and down;
   a sample rotating motor for rotating the sample rotating device; and
   a driving motor for moving the sample rotating device in a direction of an imaginary line linking the CT beam transmission part and the detector.

2. The computed tomography apparatus as claimed in claim 1, further comprising:
   an operating part for moving the CT beam transmission part and the detector up and down, rotating the sample rotating device, and transmitting the CT beam; and
   a display part for displaying a data detected by the detector.

3. The computed tomography apparatus as claimed in claim 1, wherein the main body and the first and second supporting members are made of a heatproof, a wetproof, and a shock-resistant rock, thereby eliminating an vibration phenomenon and increasing an accuracy thereof.

* * * * *